United States Patent [19]

Ballou

[11] Patent Number: 5,049,373

[45] Date of Patent: Sep. 17, 1991

[54] METHOD FOR SELECTION OF PRIMATE TUMOR-ASSOCIATED ANTIGENS SUITABLE AS IN VIVO TARGETS FOR ANTIBODIES

[75] Inventor: Byron T. Ballou, Pittsburgh, Pa.

[73] Assignee: University of Pittsburgh, Pittsburgh, Pa.

[21] Appl. No.: 533,166

[22] Filed: Jul. 13, 1990

Related U.S. Application Data

[60] Division of Ser. No. 295,775, Jan. 11, 1989, Pat. No. 4,978,520, which is a continuation-in-part of Ser. No. 906,161, Sep. 11, 1986, Pat. No. 4,798,719.

[51] Int. Cl.$^5$ ..................... G01N 33/53; A61K 39/00
[52] U.S. Cl. ..................... 424/1.1; 436/547; 436/548; 424/85.8; 424/85.91
[58] Field of Search ............ 424/1.1, 85.8, 85.91, 424/9; 436/543, 547, 548; 530/412, 413

[56] References Cited

U.S. PATENT DOCUMENTS 4,065,552 12/1977 Costa ..................................... 424/1.1
4,279,884 7/1981 Bradwell et al. ..................... 424/1.1
4,448,890 5/1984 Smetana et al. ................. 436/547 X

*Primary Examiner*—John S. Maples
*Attorney, Agent, or Firm*—Reed Smith Shaw & McClay

[57] ABSTRACT

The present invention is a process for the selection of antigens which are suitable targets for in vivo antibody localization in human tumors or other altered (or diseased) tissue. The process provides a simplified and rapid technique for discovering useful in vivo targets for antibodies and is useful in cancer detection and therapy in humans or other primates, whether or not the antigens are specific to tumors. More specifically, the invention relates to a process for the selection of antigens suitable as targets for antibodies which localize in a tumor in vivo in which antibodies are first prepared distinguishable from those present in the animal in which biofiltration is to occur and that bind to antigens present in the tumor to be targeted. These antibodies are then injected into a non-tumor-bearing primate, into a tumor-bearing animal, and into a non-tumor bearing animal of the same species as the tumor-bearing animal to permit biofiltration of the antibodies. The biofiltered antibodies are next recovered from each of the non-tumor-bearing primate, the tumor-bearing animal, and the non-tumor-bearing animal and are employed to identify antigens whose antibodies are not retained in vivo in the primate and the non-tumor-bearing animal. The antibodies that are not retained in vivo by the non-tumor-bearing primate and the non-tumor bearing animal are then compared with those antibodies that are actually retained in vivo in the tumor-bearing animal to identify the antigens corresponding to those antibodies that are selectively retained in the tumor-bearing animal. In an alternative process, the tumor-bearing animal may be replaced by a perfusable surgically removed human organ bearing a tumor, and the non-tumor-bearing animal may be replaced by a surgically removed normal organ. Passage through a primate, however, remains the method of choice for selecting antigens whose antibodies are unabsorbed in vivo.

7 Claims, 3 Drawing Sheets

5,049,373

METHOD FOR SELECTION OF PRIMATE TUMOR-ASSOCIATED ANTIGENS SUITABLE AS IN VIVO TARGETS FOR ANTIBODIES

ACKNOWLEDGEMENT

The invention described herein was made in part with the use of intramural research funds from the United States Veterans Administration.

CROSS-REFERENCE TO RELATED APPLICATION

This is a divisional of copending application(s) Ser. No. 07/295,775 filed on 1/11/89, now U.S. Pat. No. 4,978,520, which in turn is a continuation-in-part of U.S. Pat. application Ser. No. 06/906,161, filed Sept. 11, 1986, now U.S. Pat. No. 4,798,719.

FIELD OF THE INVENTION

The present invention relates to a process for the selection of antigenic targets which can serve for selective in vivo localization of tumor-localizing antibodies in primates, including humans.

BACKGROUND OF THE INVENTION

The use of appropriately labeled antibodies for tumor location has been suggested in the literature for many years (D. Pressman and G. Keighley, *J. Immunology* 59, 141 (1948); reviewed in D. Pressman, *Handbook of Cancer Immunology*, H. Waters Ed. (Garland STPM, New York, 1978) Vol. 5, pp. 29–50). However, the difficulty of obtaining reproducible, tumor-specific antibodies has markedly hindered advances in this area.

It has been demonstrated that monoclonal antibodies can give improved tumor location, partly because of the absence of interfering non-specific antibodies, and partly because of the high specificity and absence of cross-reactivity available in monoclonal antibodies (Ballou et al., *Science* 206, 844 (1979)). However, successful targeting using monoclonal antibodies in animals and humans has generally been disappointing. It is believed that the principal reason for such disappointing results has been the generally accepted assumption that monoclonal antibodies which are specific to tumors, and not to normal tissue, are required. Producing such antibodies has proved difficult and few, if any, have been found in spite of extensive research investigators in the area.

It has recently been demonstrated that absolute specificity to tumors is not necessary for proper tumor location (Ballou et al., *J. Immunology* 132, 2111–2116 (1984)). In that publication, a monoclonal antibody to a target present at much higher levels in normal tissues than in tumors was shown to localize specifically in tumors and not in the antigenic normal tissues.

In vitro and in vivo specificity are quite different as indicated by two different findings:

First, monoclonal antibodies which localize in tumors need not be truly tumor specific: examples of such antibodies are A2B5 (Reintgen et al., *J. Surg. Oncol.* 23, 205–211 (1983)) and anti-SSEA-1 (Ballou et al., *J. Immunology*, 132, 2111–2116 (1984)).

Second, antibodies which show a high level of in vitro specificity may not localize effectively. Mann et al., (*Cancer* 54, 1318 (1984)) discloses monoclonal antibodies having an apparent specificity for each of two human tumors. The expectation was that, when the tumors were implanted in a living animal, and the antibodies were radiolabeled differently so as to enable them to be distinguished from each other, then each antibody would go only to the appropriate tumor. The results, however, showed that neither antibody localized to any appreciable extent.

Thus antibodies which target tumors selectively need not be specific, and antibodies which are apparently specific may not target.

In spite of these findings, tumor-localizing antibodies have been prepared by selecting monoclonal antibodies that are more highly bound to tumors than to normal tissues in in vitro screening assays. The present invention is for a novel selection methodology, which permits analysis of a wider range of antigens than are selectable by in vitro screening.

The present invention was developed to permit selection of antigens that are selectively targeted in tumors of primates, including humans, by biofiltration methodology, while avoiding the ethically dubious injection of antibodies to human tumors into humans.

SUMMARY OF THE INVENTION

The subject invention is a process for the selection of antigens suitable as targets for antibodies which localize in a tumor in vivo comprising:

(a) preparing antibodies distinguishable from those present in the animal in which biofiltration is to occur and that bind to antigens present in the tumor to be targeted;

(b) injecting the prepared antibodies into a non-tumor-bearing primate, a tumor-bearing animal, and a non-tumor bearing animal of the same species as the tumor-bearing animal to permit biofiltration of the antibodies;

(c) recovering the biofiltered antibodies from each of the non-tumor-bearing primate, the tumor-bearing animal and the non-tumor-bearing animal;

(d) identifying antigens whose antibodies are not retained in the non-tumor-bearing primate and in the non-tumor-bearing animal using the recovered biofiltered antibodies; and (e) comparing the antibodies that are not retained in vivo by the non-tumor-bearing primate and the non-tumor-bearing animal with those antibodies that are actually retained in the tumor-bearing animal to identify the antigens corresponding to those antibodies that are selectively retained in the tumor-bearing animal.

The invention is based on the known extensive antigenic cross-reactivities among homologous proteins of higher primates. Because of this antigenic homology, it is possible to prepare antibodies against human tumors, then test for absorption in primates (e.g., rhesus monkeys, chimpanzees, orangutans). The antibodies are injected into the primate, then blood is harvested after an appropriate interval. Serum or plasma is prepared from the blood samples, and the antibody specificities that are absorbed by the primate are determined by an appropriate method (e.g., "Western" immunoblotting). This step determines those antigens whose antibodies remained unabsorbed in the primate, and would therefore be putatively unabsorbed by humans.

That antigens exist in the primate in biochemical forms and in anatomical locations similar to those found in humans can be demonstrated by immunoblotting using primate and human tissues, and staining the immunoblots with antibodies before and after biofiltration.

Immunomicroscopic staining of similar tissue sections from the primate and human, again using the biofiltered antibodies, would allow confirmation of similar anatomical locations.

The invention permits selection of those antigens whose antibodies are unabsorbed in normal humans, but are absorbed by tumors. The invention further relates to a process for the in vivo selection of antigens suitable as targets for antibodies which localize in tumors in human organs involving the use of a tumor-bearing human organ. Since primate tumors will only rarely be available, tumors suitable for absorption may include either human tumors that have been xenografted to nude mice or other animals, or tumors that have been removed from a patient in such a way as to allow ex vivo perfusion. As an opportune example of the latter method, an entire tumor-bearing kidney is usually removed during surgery for kidney cancer. The tumor-bearing kidney may be mounted on a suitable perfusion apparatus (routinely used for kidney transplantation) and antibodies added to the perfusion solution, then the perfusate tested for absorption of antigenic specificities.

DETAILED DESCRIPTION OF THE INVENTION

Figure 1:
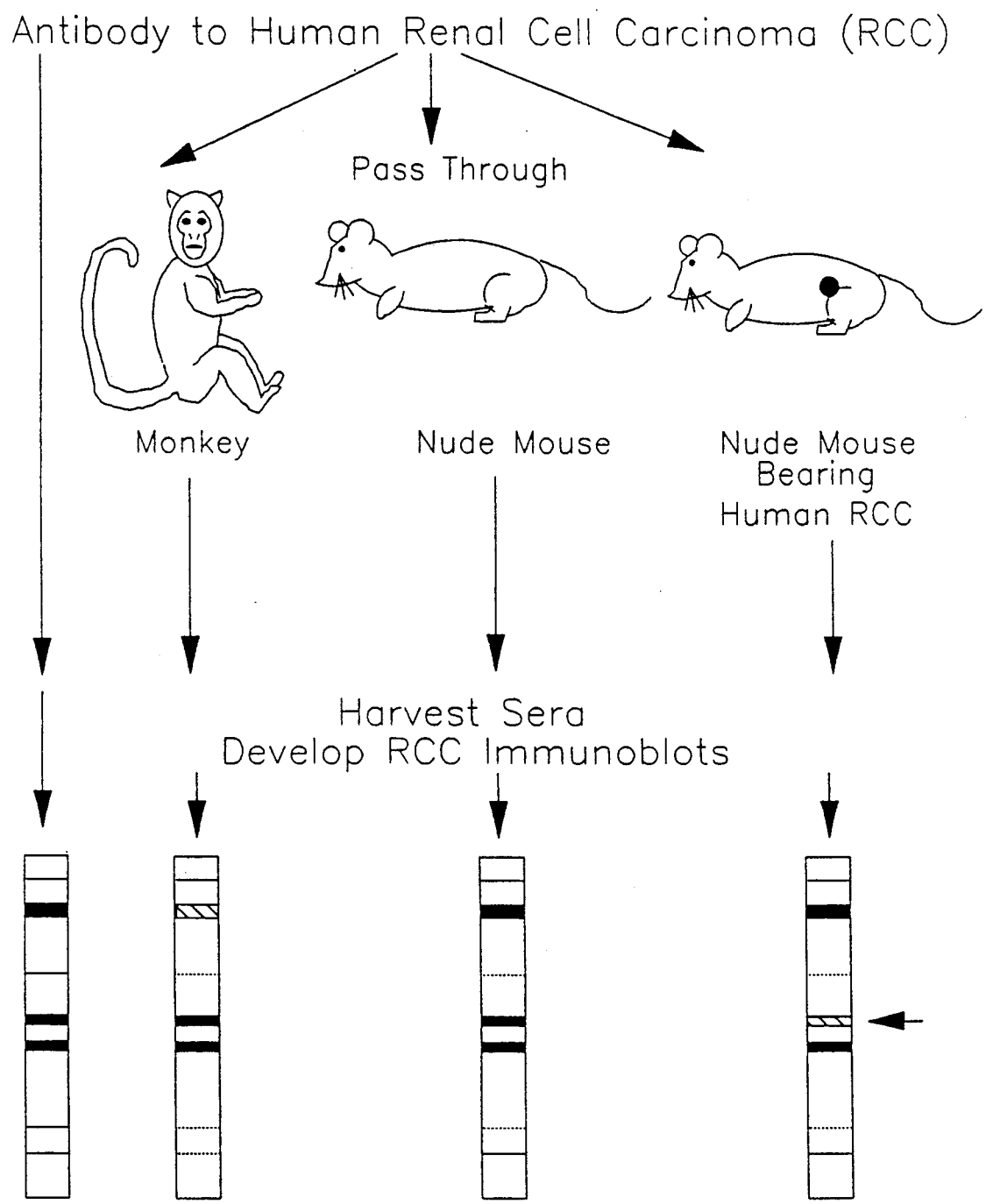
FIG. 1 is a depiction of one embodiment of the process of the invention to identify antigens to human renal cell carcinoma.

In a first embodiment of the invention as depicted by FIG. 1, the selection of antigenic specificities in primate models is, preferably, performed by the following steps:

1. Antibodies, preferably xenogeneic antibodies distinguishable from those of the animals in which biofiltration is to be performed, are prepared to the tumor of interest by immunizing animals.
2. Antibody-containing fractions (immunoglobulins) are purified from the sera of the immunized animals.
3. The purified immunoglobulins in appropriate amounts are injected into the circulation of a normal, non-tumor bearing primate, such as a rhesus monkey, a normal non-tumor bearing animal, and a tumor-bearing animal of the same species as the non-tumor-bearing animal; any antibodies which can be absorbed ("biofiltered") will be removed in this step.
4. After a suitable time interval, preferably between 8 and 36 hours, a sample of serum from each of the non-tumor bearing primate, the non-tumor bearing animal, and the tumor-bearing animal injected in (3) is removed; these sera contain the "biofiltered" antibodies.
5. The biofiltered antibody is then used to identify biochemically the antigens corresponding to the biopurified antibodies by known methods.

The antigens of interest are those whose corresponding antibodies are unabsorbed by the primate and the non-tumor-bearing animal, but are absorbed by the tumor-bearing animal.

Among the biochemical methods which may be used are gel blots, immunoprecipitation, and solid-phase adsorption of tumor substances. Preferably, gel blotting is used. These biochemical methods can be used by employing a second antibody specific to antibodies from the originally immunized animal.

6. Confirmation that the antibodies do define a specificity suitable for in vivo targeting is done by (a) selecting specific antibodies defined by biofiltration, (b) radiolabeling the selected antibodies, then (c) injecting the radiolabeled, selected antibodies into tumor-bearing animals.
7. The antigens defined by these biofiltered polyclonal antibodies may be purified and then used as immunogens for preparation of monoclonal antibodies in accordance with known methods, such as the method of Damsky et al., Cell 34, 355–366, 1983, the disclosure of which is incorporated herein by reference. An important feature in testing the monoclonal antibodies is competition with the polyclonal antibodies isolated in steps 1-6 described above, thus ensuring that the monoclonal antibodies are directed to the same antigens as the biopurified polyclonals.

Figure 2:
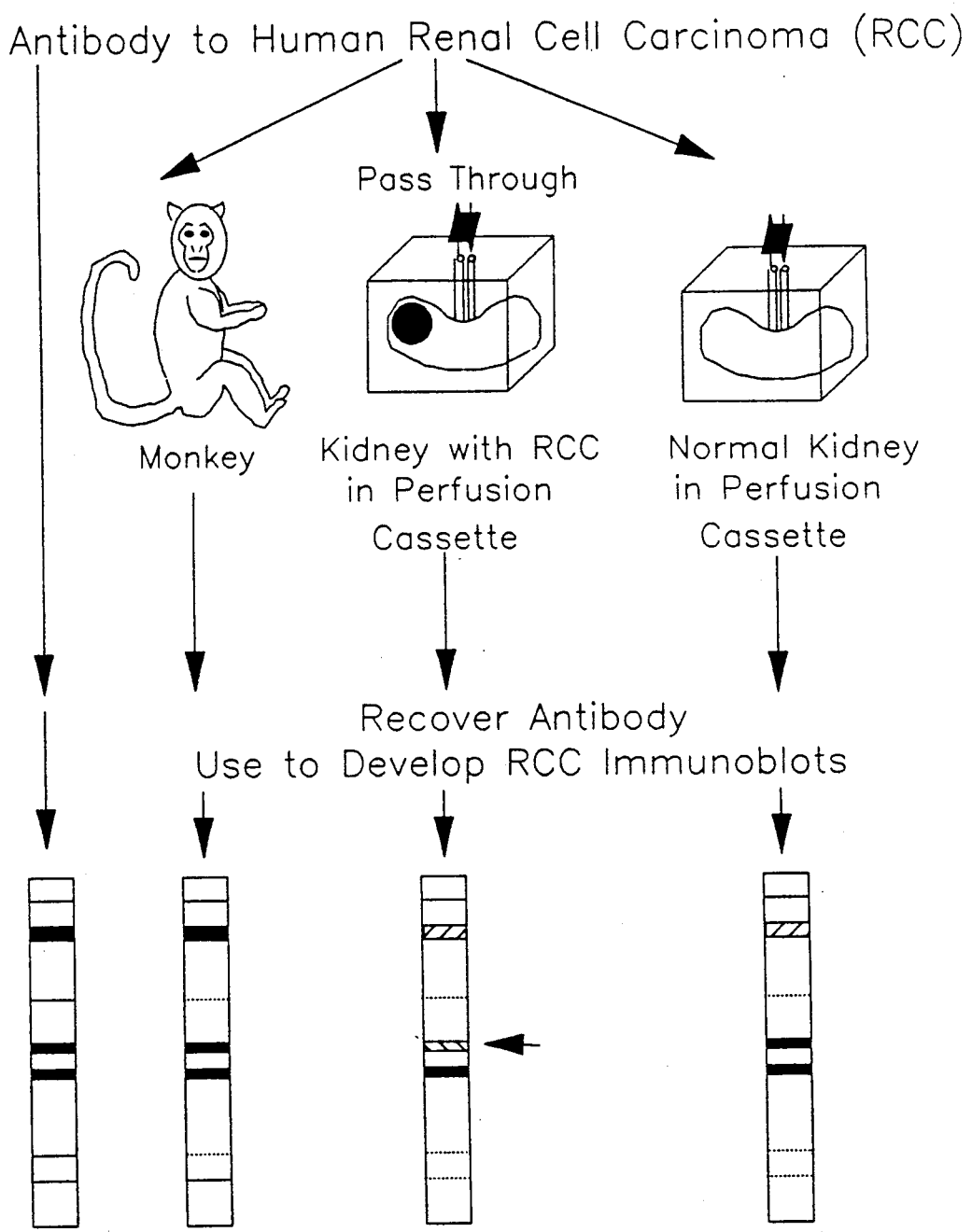
FIG. 2 is a depiction of a second embodiment of the process of the invention to identify antigens to human renal cell carcinoma.

In a further embodiment of the invention as depicted by FIG. 2, the selection of antigenic specificities is performed by the following steps:

1. Antibodies, preferably xenogenic antibodies, distinguishable from those of the animals in which biofiltration is to be performed and distinguishable from components of the perfusion fluids to be used, are prepared by immunizing animals.
2. Antibody-containing fractions (immunoglobulins) are purified from the sera of the immunized animals.
3. The purified immunoglobulins in appropriate amounts are injected into the circulation of a normal, non-tumor-bearing primate, such as a rhesus monkey, and into the perfusion fluid of a human tumor that has been surgically removed so as to allow perfusion of the tumor (for example, a whole kidney is normally removed when the kidney bears a renal cell carcinoma; the removed kidney may be mounted in a perfusion apparatus of the sort normally used for preserving kidneys for transplantation).
4. After a suitable interval (preferably 8 to 36 hours for the primate, and 2 to 36 hours for the perfused organ, depending on perfusion volume, flow rate, and the preservation state of the organ), a sample of serum from the primate and a sample of the perfusion fluid from the perfused tumor are removed. These samples contain the "biofiltered" antibodies.
5. The biofiltered antibody is then used to identify biochemically the antigens corresponding to the biopurified antibodies by known methods. The antigens of interest are those whose corresponding antibodies are unabsorbed by the primate, but are absorbed by the tumor-bearing organ. In the most preferred technique, a normal organ corresponding to the tumor-bearing organ (e.g. from a cadaver)

will also have been perfused in a fashion identical to the tumor-bearing organ. In that case, antigens of interest will be those whose corresponding antibodies are unabsorbed by the primate and by the normal organ, but are absorbed by the tumor-bearing organ.

Among the biochemical methods which may be used are gel blots, immunoprecipitation, and solid-phase adsorption of tumor substances. Preferably, gel blotting is used. These biochemical methods can be used by employing a second antibody specific to antibodies from the originally immunized animal.

The present invention provides for at least three additional possibilities for selection of specificities suitable for tumor targeting in humans:

1. Antigen-binding fragments could be prepared from the initial whole polyclonal antibodies, then biopurification could be performed in human volunteers. The rationale is that, since such fragments lack effector regions, any chance of cell- or complement-mediated damage to humans will be avoided. Purification of antigens and preparation of monoclonal antibodies would follow as described above.
2. Prospective organ donors which cannot be used for transplantation (e.g., because of infection) could be used for biofiltration, given informed consent by next of kin.
3. Targetable human antigens may be defined by homology to targetable animal antigens. Earlier work of the inventor has shown that biofiltered antibodies to mouse tumor antigens cross-react with antigens derived from human tumors. A number of these human antigens are biochemically similar to those found in mice, and hence are probably true homologues. These antigens should, therefore, be similarly targetable in human tumors, but not in normal tissues.

EXAMPLES

Experimental Procedure

Example: Selection of antigens suitable as targets for antibodies which localize in human renal cell carcinoma (RCC) (kidney cancer) tumors 1. Immunize rabbits using human RCC extract.
2. Prepare antisera from rabbits; purify immunoglobulin fraction by column chromatography.
3. Re-inject rabbit immunoglobulins into normal primate, normal animal and animal of the same species bearing a human tumor. Antibodies which bind to normal tissues and to the tumor are absorbed.
4. After a suitable time interval, preferably 24 to 72 hours, remove serum sample from normal primate, normal animal, and tumor-bearing animal; these samples contain rabbit immunoglobulins that were not absorbed by the normal primate and normal animal and that were absorbed by the tumor.

The three serum samples are compared by standard "Western" immunoblotting. When the strips stained by rabbit antibody before biofiltration were compared with those stained with an antibody biofiltered (preferably after 8-36 hours) through a primate, a non-tumor-bearing animal, or a tumor-bearing animal, fewer antigens were detected using the biofiltered than the input antibody. The "missing" antibody specificities are those retained by the primate or the other animals.

6. The antibodies which remain after biofiltration through the primate and through the normal animal, but not through the tumor-bearing animal, define antigens suitable for tumor targeting in humans. To show that these antibodies actually will target a tumor, the antigens are purified, then used to prepare monospecific antibodies by affinity chromatography. These selected antibodies are radiolabeled and injected into normal and tumor-bearing animals or perfused through normal and tumor-bearing organs.
7. Those antibodies which concentrate in the tumors will define antigens suitable as targets. Antigens corresponding to the antibodies which successfully targeted tumors may be used as immunogens for preparation of monoclonal antibodies.

It should also be possible to "bootstrap" purification of antigens by (a) purification of a small amount of antigen; (b) immunization using the purified antigen; and (c) repeat purification using the now relatively monospecific antibody.

Example 1

Rabbit antisera to human renal cell carcinoma (RCC) were developed by repeated immunizations at biweekly intervals using the whole tumor homogenized in saline (1 mg protein/immunization). All immunizations were subcutaneous; the first using 1:1::tumor homogenate:Freund's complete adjuvant, while all subsequent immunizations were done using the same proportion of Freund's incomplete adjuvant. After six months, rabbits were bled and serum was fractionated by standard techniques. The IgG fraction was isolated by gel filtration chromatography on Sephacryl S-200 (Pharmacia).

The r Rabbit antibodies were passaged through a rhesus monkey by intraveneous injection; the animal was bled twelve hours later, and serum prepared from the whole blood. Antibody was also passaged similarly through a nude mouse, and through a nude mouse bearing a human kidney tumor. The recovered sera were diluted in 10% fetal calf serum in Dulbecco's PBS, then incubated overnight on sections of a "Western blot" of a Laemmli SDS gel prepared using the human renal cell carcinoma. After overnight incubation, the blots were washed using 0.05% Tween 20 in tris-buffered saline, then incubated with 1/500 peroxidase-conjugated goat antibody to rabbit IgG (obtained from Organon Technica) for three hours at room temperature. The blots were re-washed to remove unabsorbed antibody, then developed using 4-chloro-1-naphthol using the procedures described in Allen, R. C., Saravis, C. A., and Maurer, H. R. (1984) *Gel Electrophoresis and Isoelectric Focusing of Proteins*. New York: Walter de Gruyter, pp. 222-225, the disclosure of which is incorporated herein by reference.

Figure 3:
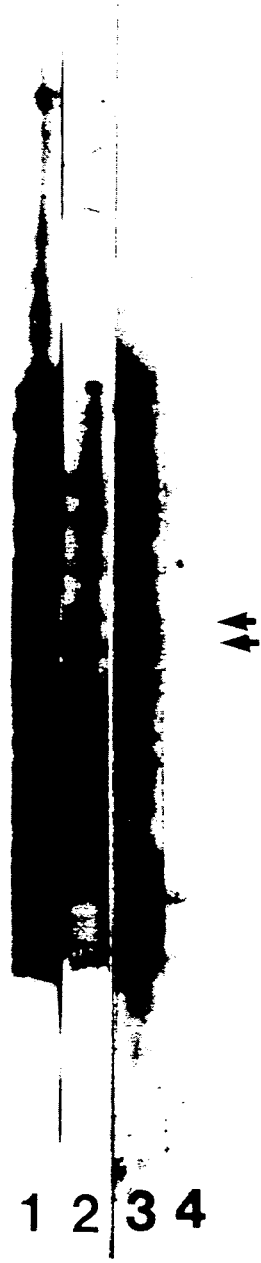
FIG. 3 is a photograph of strips cut from a Western Blot of a whole unbiofiltered antibody: (#1), antibody biofiltered through a rhesus monkey (#2), antibody biofiltered through a nude mouse (#3) and antibody biofiltered through a nude mouse bearing a human renal carcinoma (RCC) tumor (#4). The two arrows indicate antigens whose corresponding antibodies were unabsorbed by the rhesus monkey and the nude mouse, but were absorbed by the nude mouse bearing the human RCC tumor.

FIG. 3 shows the results from this test using rabbit antibodies developed to a human renal cell carcinoma. All results are from an SDS-Western Blot of the original human kidney tumor. The figure shows four strips from an immunoblot labeled using (1) whole antibody before injection; (2) antibody after passage through rhesus monkey; (3) antibody after passage through a normal nude mouse; and (4) antibody after passage through a nude mouse xenografted with a human tumor. The two arrows indicate two specificities whose antibodies were unabsorbed by monkeys and by a normal nude mouse, but were absorbed by a nude mouse bearing a human tumor.

Although the invention has been described in detail for the purposes of illustration, it is to be understood that such detail is solely for that purpose and that variations can be made therein by those skilled in the art without departing from the spirit and scope of the invention except as it may be limited by the claims.

What is claimed is:

1. A process for the selection of antigens suitable as targets for antibodies which localize in tumors in humans in vivo comprising:
   (a) preparing antibodies that bind to antigens present in a human tumor;
   (b) injecting the prepared antibodies into a non-tumor-bearing primate and into the perfusion fluid of a perfused human tumor;
   (c) recovering the biofiltered antibodies from each of the non-tumor-bearing primate and the perfused human tumor;
   (d) identifying antigens whose antibodies are not retained in vivo in the non-tumor-bearing primate but are retained by the perfused human tumor; and
   (e) comparing the antibodies to determine which specificities are not retained in vivo by the non-tumor-bearing primate, but are retained in the perfused human tumor, to identify the antigens corresponding to those antibodies retained only in the perfused human tumor.

2. The process of claim 1 wherein the screening in step (e) further comprises selecting specific antibodies which survive the biopurification of step (b), radiolabeling the selected antibodies and injecting the radiolabeled selected antibodies into the human tumor.

3. The process of claim 1 wherein antigens whose antibodies are not retained in the non-tumor-bearing primate, but are retained in the perfused human tumor, are identified in step (d) by a biochemical method.

4. The process of claim 3 wherein antigens whose antibodies are not retained in the non-tumor-bearing primate, but are retained in the perfused human tumor, are identified in step (d) using a biochemical method selected from the group consisting of Western blots, immunoprecipitation and solid-phase adsorption.

5. The process of claim 1 wherein the antibodies prepared in step (a) are xenoantibodies.

6. The process of claim 5 wherein the antibodies prepared in step (a) are polyclonal xenoantibodies.

7. The process of claim 5 further comprising:
   (f) preparing monoclonal antibodies using the antigen identified in step (e) as immunogens.

* * * * *